(12) United States Patent
Ricotta et al.

(10) Patent No.: US 7,351,258 B2
(45) Date of Patent: Apr. 1, 2008

(54) APPARATUS AND METHOD FOR FIXATION OF VASCULAR GRAFTS

(75) Inventors: John Ricotta, Setauket, NY (US); Benjamin S. Hsiao, Setauket, NY (US); Rajesh H. Somani, Upton, NY (US)

(73) Assignee: The Research Foundation of State University of New York at Stony Brook, Stony Brook, NY (US)

( * ) Notice: Subject to any disclaimer, the term of this patent is extended or adjusted under 35 U.S.C. 154(b) by 473 days.

(21) Appl. No.: 10/501,066

(22) PCT Filed: Apr. 18, 2002

(86) PCT No.: PCT/US02/12136

§ 371 (c)(1),
(2), (4) Date: Jan. 5, 2005

(87) PCT Pub. No.: WO02/085254

PCT Pub. Date: Oct. 31, 2002

(65) Prior Publication Data

US 2005/0102024 A1    May 12, 2005

(51) Int. Cl.
*A61F 2/06* (2006.01)
(52) U.S. Cl. .................... 623/1.36; 623/1.23
(58) Field of Classification Search ........... 623/1.36, 623/1.23
See application file for complete search history.

(56) References Cited

U.S. PATENT DOCUMENTS

| | | | |
|---|---|---|---|
| 5,360,443 A * | 11/1994 | Barone et al. ............. 623/1.13 |
| 5,720,755 A | 2/1998 | Dakov | |
| 5,720,776 A * | 2/1998 | Chuter et al. ............. 623/1.36 |
| 5,843,169 A | 12/1998 | Taheri | |
| 5,968,053 A | 10/1999 | Revelas | |
| 6,193,745 B1 * | 2/2001 | Fogarty et al. ............ 623/1.12 |
| 6,312,457 B1 * | 11/2001 | DiMatteo et al. .......... 623/1.13 |
| 6,416,522 B1 * | 7/2002 | Strecker .................... 606/143 |
| 6,702,844 B1 * | 3/2004 | Lazarus ..................... 623/1.14 |
| 6,911,035 B1 * | 6/2005 | Blomme .................... 606/153 |

FOREIGN PATENT DOCUMENTS

| | | |
|---|---|---|
| WO | 99/55254 | 11/1999 |
| WO | 00/16701 | 3/2000 |

* cited by examiner

*Primary Examiner*—Ehud Gartenberg
*Assistant Examiner*—Jason-Dennis Stewart
(74) *Attorney, Agent, or Firm*—The Farrell Law Firm, PC

(57) ABSTRACT

An apparatus for facilitating securement of a vascular graft within a blood vessel, includes a shaft dimensioned for passage within a blood vessel and having an expansion member movable between a contracted condition and an expanded condition and a fastener array comprising at least one fastener disposed about a peripheral portion of the expansion member. The one fastener is deployable into a wall of the blood vessel upon movement of the expansion member to the expanded condition thereof, to thereby engage the vascular graft to secure the vascular graft to a wall of the blood vessel. The fastener array preferably includes a plurality of fasteners. The fasteners may be operatively connected to each other and releasably secured to the peripheral portion of the expansion member.

20 Claims, 18 Drawing Sheets

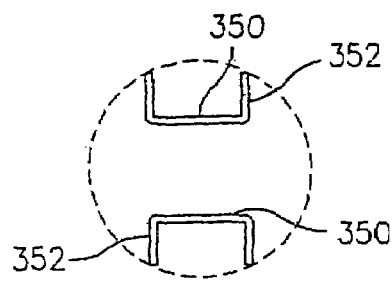
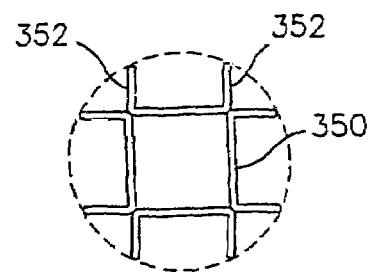
FIG. 11A  FIG. 11B
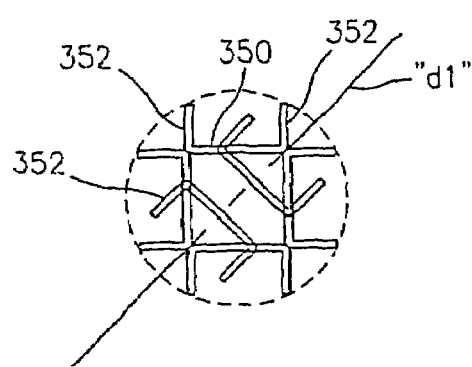
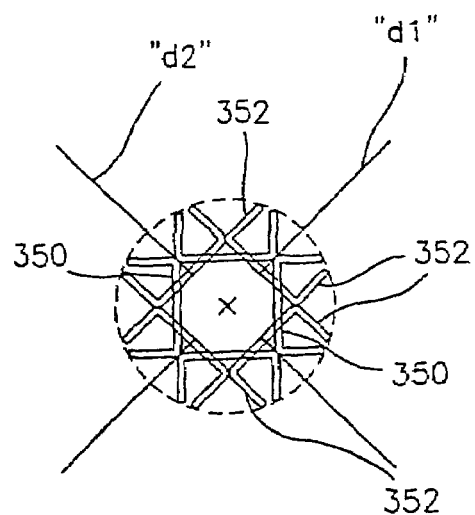
FIG. 11C  FIG. 11D

APPARATUS AND METHOD FOR FIXATION OF VASCULAR GRAFTS

FIELD OF INVENTION

The present invention relates generally to systems and methodologies for securing a graft to a body vessel, and, more particularly, to an intralumenal surgical apparatus and associated method of use for facilitating introduction and securement of a vascular graft prosthesis within a blood vessel.

BACKGROUND OF THE INVENTION

Endovascular grafts have been developed to treat patients with arterial lesions, particularly, aneurysms, trauma and arterial dissections, from within the arterial tract to reduce morbidity and mortality associated with the arterial disorder. Application of the graft is typically performed in conjunction with a minimally invasive operative procedure to minimize patient trauma, recovery time, etc.

A variety of endovascular grafts are currently on the market or in clinical trails. These grafts have a number of different characteristics related to their fixation mechanisms, construction and support with respect to the vessel wall. Currently, fixation of the endovascular graft can be achieved through radial wall tension using a self expanding stent or by balloon expansion of a deformable stent which may possess fixation elements to penetrate the arterial wall. Alternatively, the stent/graft may be secured to the vessel wall through suturing.

U.S. Pat. No. 4,787,899 to Lazarus discloses an intralumenal grafting system for placement of a hollow graft in a corporal lumen. The '899 system incorporates a cylindrically shaped graft having a plurality of hook-like staples embedded in the graft. Once the graft is positioned with the desired location in the vessel, an inflation member is expanded to drive the staple legs through the vessel wall thereby securing the graft to the vessel wall.

However, known graft deployment systems such as the type disclosed in the '899 patent are subject to several disadvantages which detract from their usefulness in vascular graft securement. Graft migration subsequent to deployment and leakage about the staple-vessel wall juncture, sometimes in the order of 20-30%, are typical with such systems. In addition, the graft with fixed staple arrangement is deficient in conformational changes which may occur after grafting. With modular grafts, i.e., multiple element grafts connected to each other, late disruption at the connection between the components is also prevalent.

SUMMARY OF THE INVENTION

Accordingly, the present invention is directed to a system and method which overcomes the disadvantages of the prior art by substantially minimizing graft dislodgement and leakage associated with the fixation mechanism. In one preferred embodiment, an apparatus for facilitating securement of a vascular graft within a blood vessel includes a shaft dimensioned for passage within a blood vessel, an expansion member mounted to the shaft and being movable between a contracted condition and an expanded condition, and a fastener array comprising at least one fastener disposed about a peripheral portion of the expansion member. The one fastener is deployable into a wall of the blood vessel upon movement of the expansion member to the expanded condition thereof, to thereby engage the vascular graft to secure the vascular graft to the blood vessel wall. The fastener array may include a plurality of fasteners positioned to define a substantially annular configuration whereby the fasteners are arranged about the periphery of the expansion member. The fasteners may be operatively connected to each other and releasably secured to the periphery portion of the expansion member with, e.g., an adhesive and are preferably released from each other after they are deployed. In accordance with an alternate embodiment, the fasteners of the fastener array are connected to a biocompatible member which is mounted about the periphery of the expansion member. The biocompatible member may be a biocompatible tape to which the fasteners are adhered. The fasteners of the fastener array may each be a surgical staple having a base and penetrating legs extending from opposed ends of the base. Preferably, the legs of each staple define a length sufficient to penetrate through the vascular graft and lodge within the blood vessel wall without penetrating completely through the blood vessel wall.

In another alternate embodiment, the apparatus includes an elongated shaft dimensioned for passage within a blood vessel, an expansion member supported at a distal end of the elongated shaft and being adapted to expand from a substantially contracted condition to a substantially expanded condition, and a surgical staple array including a plurality of surgical staples arranged about a peripheral portion of the expansion member. At least first and second adjacent surgical staples of the staple array are arranged in partial overlapping relation. The staples are deployable into a wall of a blood vessel upon expansion of the expansion member to the expanded condition thereof. Thus, when the expansion member and the surgical staple array are positioned within a substantially tubular graft disposed within the blood vessel, the expansion member is expanded to the expanded condition to deploy the surgical staples thereby causing engagement of the surgical staples with the vascular graft and the blood vessel wall to secure the vascular graft within the blood vessel.

A method for securing a vascular graft within a blood vessel is also disclosed. The method includes the steps of accessing a blood vessel; positioning a vascular graft at a predetermined location within the blood vessel; introducing a fastener array including a plurality of surgical fasteners arranged about a longitudinal axis of the fastener array within the blood vessel and moving the fastener array within the blood vessel to a position at least partially disposed within the vascular graft; and deploying the surgical fasteners of the fastener array radially outwardly relative to the longitudinal axis whereby penetrating portions of the surgical fasteners penetrate the vascular graft and engage a wall of the blood vessel without completely penetrating through the blood vessel wall, to thereby secure the vascular graft to the blood vessel wall. The vascular graft may be a substantially tubular vascular graft defining an outer peripheral graft wall. The surgical fasteners of the fastener array are arranged with respect to each other to define a substantially annular configuration whereby, during the step of deploying, the surgical fasteners secure the substantially tubular graft to the blood vessel substantially along the outer peripheral graft wall.

BRIEF DESCRIPTION OF THE DRAWINGS

Preferred embodiments of the present invention are described herein with reference to the drawings wherein:

FIGS. 11A-11G are schematic views illustrating alternate embodiments of the staple array of FIG. 3;

DETAILED DESCRIPTION OF THE PREFERRED EMBODIMENTS

The preferred embodiments of the apparatus and method disclosed herein are discussed in terms of repair of a blood vessel wall with application of a vascular graft, preferably, an endovascular graft. The preferred embodiment has particular application in treating vascular lesions such as aneurysms. It is envisioned, however, that the disclosure is applicable to a wide variety of procedures where a graft prosthesis is utilized to repair or support a vessel wall. In addition, it is believed that the present apparatus and method finds application in both open and minimally invasive procedures.

The following discussion includes a description of a system utilized in application of a vascular graft followed by a description of the preferred method for securing the graft within a vascular body utilizing the system.

In the discussion which follows, the term proximal, as is traditional, will refer to the portion of the system which is closest to the operator while the term distal will refer to the portion which is furthest from the operator.

Figure 1:
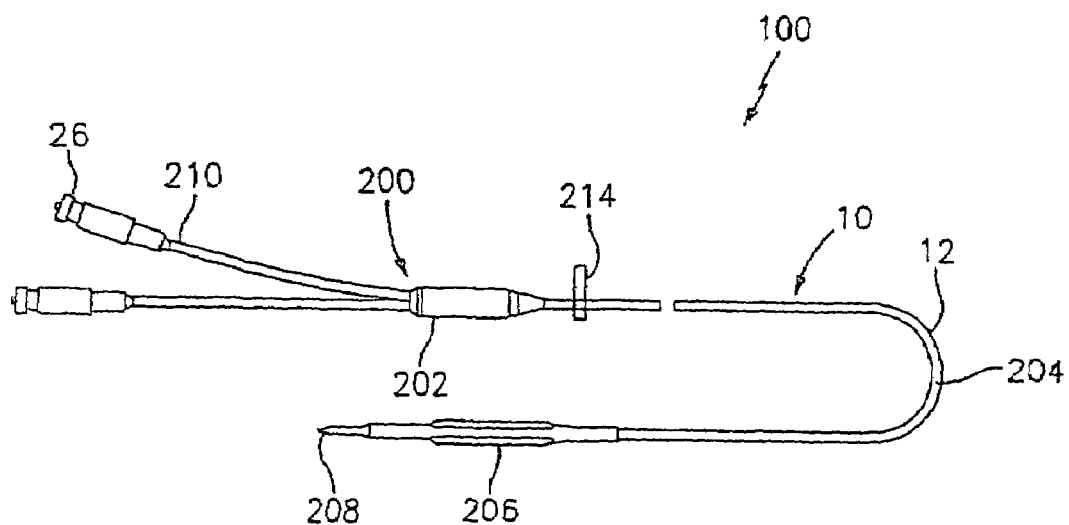
FIG. 1 is a view of the system for fixation of an endovascular graft in accordance with the principles of the present invention.

Referring now to the drawings in which like reference numerals identify similar or identical elements throughout the several views, FIG. 1 illustrates the system for deployment of a vascular graft in accordance with the principles of the present disclosure. The system is particularly intended to be used in conjunction with a minimally invasive procedure wherein access to the operative site is limited or inaccessible by means of conventional techniques. System 100 includes catheter apparatus 200 and a staple array 300 mounted to the catheter apparatus 200. Generally, catheter 200 includes handle 202, elongated catheter shaft 204 extending distally from the handle 202 and catheter balloon 206 mounted at the distal end of the catheter shaft 204. Catheter shaft 204 is generally preferably flexible to follow the tortuous path through the body vessel and has a distal blunt end 208 to minimize the potential of undesired penetration into tissue.

Catheter balloon 206 is preferably inflatable between a non-expanded condition and an expanded condition. Catheter balloon 206 may be fabricated from any conventional balloon material such as thermoplastic elastomers, polyethylene terephthalate (PET), ethylene-butylene-styrene block copolymers, etc. An inflation port 210 adjacent handle 202 permits introduction of inflation fluids into catheter 200 to inflate catheter balloon 206. Inflation port 210 is in fluid communication with an inflation lumen extending through catheter shaft 204 and terminating in catheter balloon 206. Alternatively, catheter balloon 206 may be replaced with a mechanical expanding member which expands and contracts upon movement of corresponding mechanical elements. Apparatii incorporating such mechanical expansion means suitable for use with the system of the present invention are disclosed in U.S. Pat. No. 5,855,565 to Bar-Cohen et al. and U.S. Pat. No. 5,507,269 to Marin, the contents of each disclosure being incorporated herein by reference. As a further alternative, the expansion member may be a self expanding stent with the staples 206 mounted to/on the stent. Expansion of the stent occurs in response to temperature changes, e.g., upon exposure of the stent to body temperature.

Figure 2:
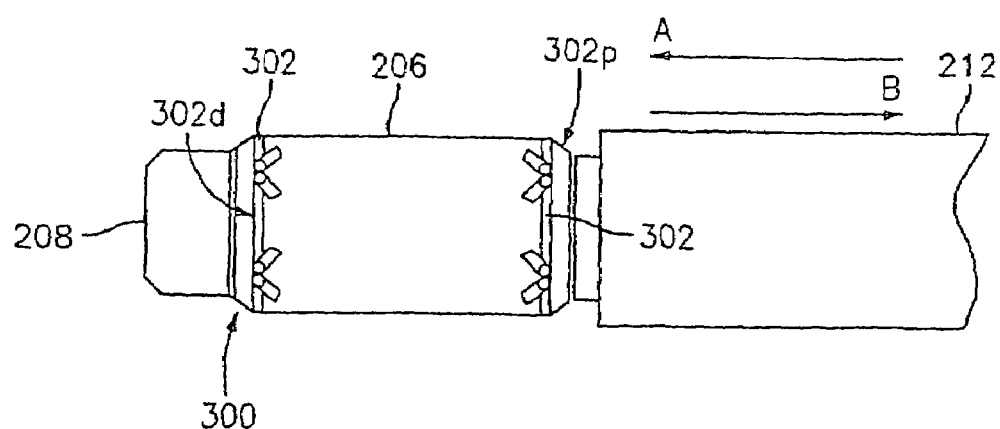
FIG. 2 is an enlarged side plan view of the distal end of the intralumenal catheter apparatus of the system of FIG. 1 illustrating the catheter balloon and staple array mounted to the catheter balloon.

As best depicted in FIG. 2, catheter 200 may further include an outer tube 212 coaxially mounted about catheter shaft 204. Outer tube 212 is adapted to reciprocally longitudinally move relative to catheter shaft 204 (in directions A and B depicted in FIG. 2) between an advanced position enclosing staple array 300 and a retracted position at least partially exposing the staple array. In FIG. 2, outer tube 212 is shown in the retracted position. In one arrangement, catheter tube 212 slides between the two positions via a push/pull motion on the proximal end of the catheter tube 212. A handle 214 represented schematically in FIG. 1 may be positioned adjacent the proximal end of catheter shaft to facilitate the desired longitudinal movement. Other means for effectuating movement of outer tube may be readily appreciated by one skilled in the art.

Figure 3:
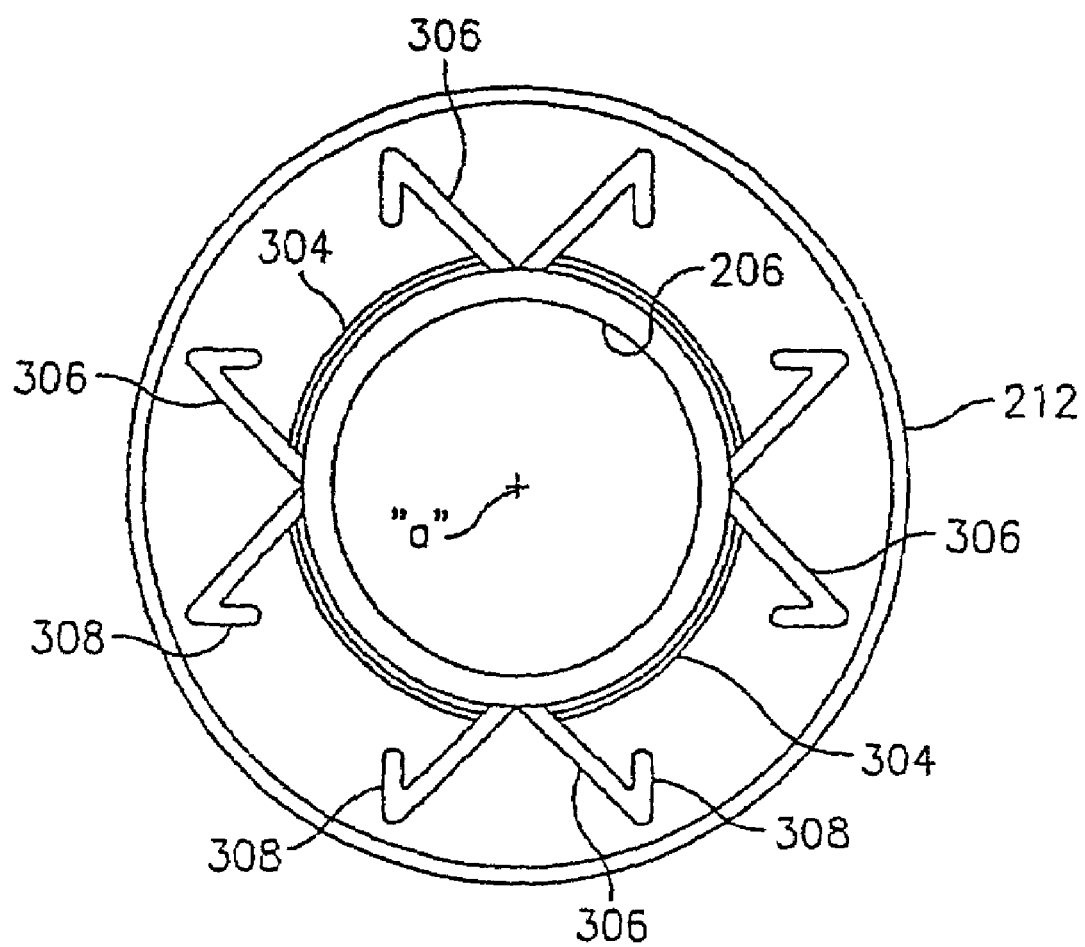
FIG. 3 is a schematic cross-sectional view illustrating the annular arrangement of the staple array about the catheter balloon.
Figure 4:
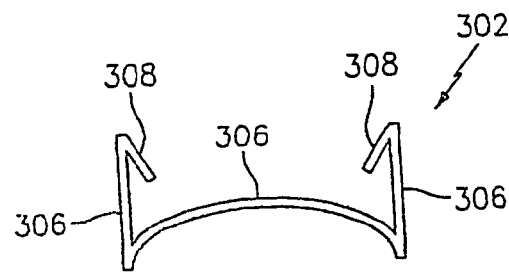
FIG. 4 is a view of a preferred staple of the staple array.

With reference now to FIGS. 2-4, staple array 300 of the system includes a plurality of staples 302 circumferentially mounted about catheter balloon 206 with a first staple set 302p adjacent the proximal end of the balloon and a second set 302d adjacent the distal end. The preferred staple 302 includes staple base 304 and staple legs 306 extending from opposed ends of the staple base 304. Staple base 304 defines an arcuate shape to preferably generally correspond to the outer dimension of catheter balloon 206. Staple legs 306 preferably define a length sufficient to penetrate the graft and enter the blood vessel wall without completely piercing the vessel wall, the significance of which will be appreciated from the description hereinbelow. Staple legs 306 may further possess a retaining element or hook 308 (FIG. 3) depending inwardly from each leg 306. Retaining hook 308 is advantageously dimensioned to securely engage the vessel wall and minimize the potential of staple 302 releasing from the wall subsequent to deployment. The overall size of the staples will depend on the number of staples to be used and the particular application. Staples are preferably made from a biocompatible material such as titanium, stainless steel, thermoplastics, etc and are characterized by possessing good wear and physical properties such as strength, flexibility and degradation.

As best depicted in FIGS. 2-3, staple array 300 defines an annular or circular arrangement about the periphery of catheter balloon 206. In one preferred embodiment, staples 302 are arranged in juxtaposed, i.e., side by side relation, with no overlapping of adjacent staples 206. Staples 302 are connected to each other preferably along the outer surfaces of the adjacent staple bases 304 and/or legs 306 to define the ring-like configuration. An adhesive, preferably, a biodegradable adhesive such as hyaluronic acid, may be utilized to connect the staples to define the array.

Staple array 300 is positioned about catheter balloon 206 with staple legs 306 extending radially outwardly relative to the axis "a" of catheter shaft 204. With this arrangement, staple legs 306 are positioned to engage the graft "g" and to extend within the body vessel to which the graft is placed. Preferably, staple array 300 is adhered to the outer surface of catheter balloon 206, e.g., the outer surface of staple base 304 of each staple 302 may be coated with the adhesive (e.g., hyaluronic acid) and mounted to the outer surface of the catheter balloon 206. The annular array of staples 302 as connected through the use of an adhesive in conjunction with adhesion of the array to the outer surface of the catheter balloon 206 stabilizes the array and ensures movement of the staple legs 306 in a general outward radial direction upon expansion of the catheter balloon 206 thereby facilitating engagement with the graft and positive fixation with respect to the vessel wall. The annular side by side arrangement of staples 302 at both the proximal and distal ends of catheter balloon 206 ensures that the vascular graft is securely attached at both ends to the interior of the vessel wall.

Figure 5A:
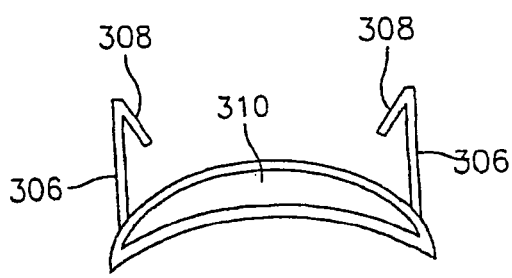
FIGS. 5A-5L illustrate various alternate embodiments of the staple of FIG. 4.
Figure 5B:
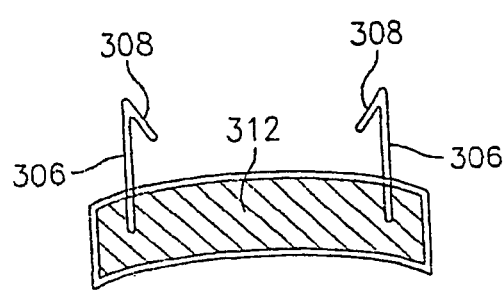
Figure 5C:
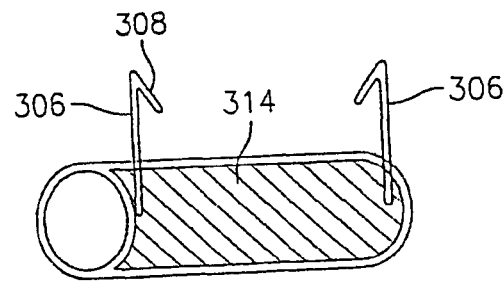
Figure 5D:
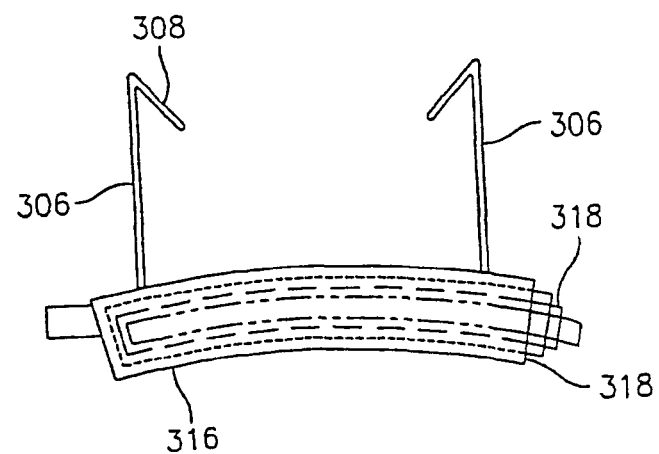
Figure 5E:
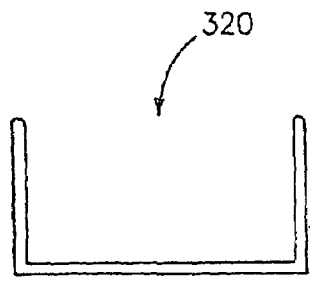
Figure 5F:
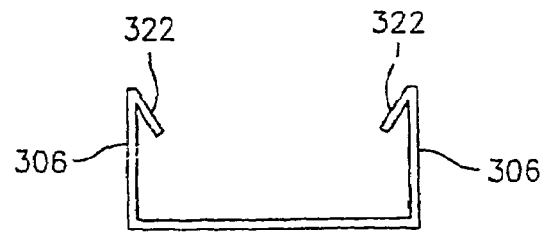
Figure 5G:
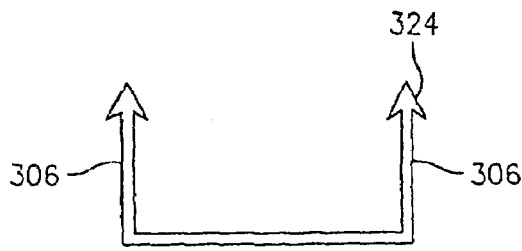
Figure 5H:
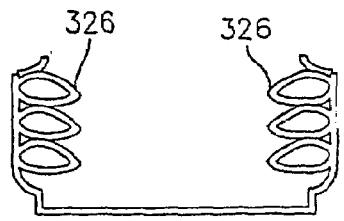
Figure 5I:
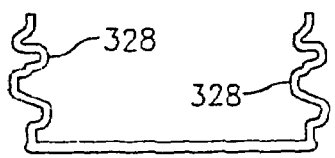
Figure 5J:
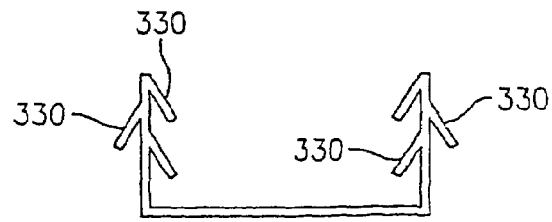
Figure 5K:
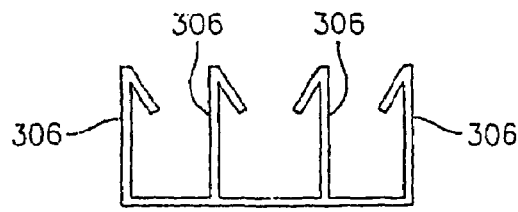
Figure 5L:
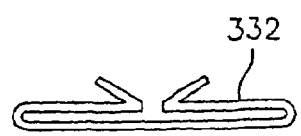

FIGS. 5A-5L illustrate alternative embodiments of the staple of FIG. 4 suitable for use with the system of the present invention. For example, the staple of FIG. 5A is substantially similar to the staple of FIG. 4, but, further includes a wide arc base 310 which engages a greater surface area of the graft and serves to further stabilize the staple with respect to catheter balloon 206 upon which it is mounted. Alternatively, the staple may have a curved rectangular base 312 or a curved cylindrical base 314 as depicted in FIGS. 5B, 5C, respectively. FIG. 5D illustrates a further alternative having a telescopic base 316 with a plurality of multiple cylindrical portions 318 coaxially arranged about the axis of the base. Upon deployment, the cylindrical portions 318 extend outwardly to circumscribe the inner wall of the body vessel. An embodiment incorporating a telescopic staple arrangement will be discussed in further detail hereinbelow. FIG. 5E details a conventional staple 320, i.e., C-shaped, which may be utilized with the system of the present invention. FIG. 5F is similar to the staple of FIG. 5E, but, further includes inclined hooks 322 on each of the staple legs obliquely arranged and depending inwardly towards the central area of the base of the staple. The hooks 322 function in a similar manner to their corresponding counterparts of FIG. 4. FIG. 5G illustrates a staple with arrow shaped hooks 324 at the ends of the staple legs which facilitate penetration through the vascular graft and vessel wall. FIG. 5H illustrates a staple with helical shaped hooks 326 which penetrate and facilitate retention of the staple within the vessel wall. FIG. 5I illustrates a staple with curved staple legs 328 while FIG. 5J illustrates a staple with multiple hooks 330. It is also envisioned that a plurality of multiple legs 306 (e.g. 4) may be incorporated within the staple as disclosed in FIG. 5K. FIG. 5L shows a staple with a folded stem 332. It is further appreciated that the staples may be replaced with other surgical fasteners including surgical tacks, nails, clips, etc.

Operation of the Apparatus

Referring now to FIGS. 6-10, operation of the system for securing an aortic graft within the aorta for treating an aortic aneurysm will be discussed. Preferably, the aortic aneurysm is accessed percutaneously through the femoral artery and the aortic graft is placed within the aneurysm. The graft is preferably fabricated from a polytetrafluoroethylene (PTFE) or polymer material as is known in the art. Preferably, the graft may be a stent/graft combination having an expandable stent and a graft coaxially positioned about the stent. The expandable stent may be self expanding or, optionally, a mechanically deformable stent such as the type disclosed in U.S. Pat. No. 6,774,328 to Cragg, the contents of which are incorporated herein by reference.

Figure 6:
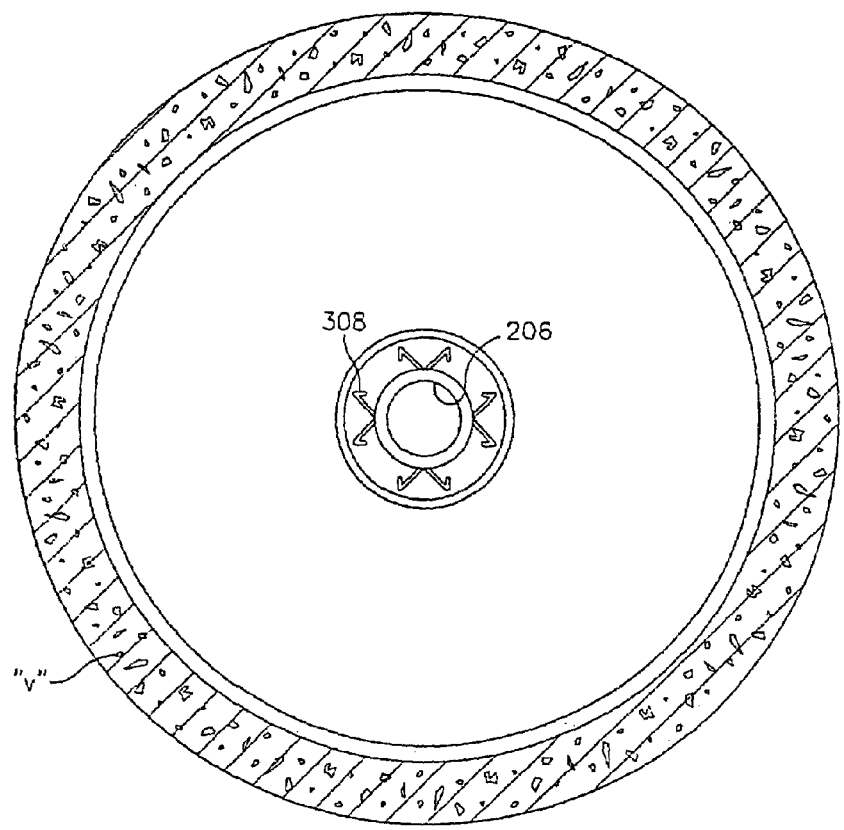
FIG. 6 is a schematic cross-sectional view similar to the view of FIG. 3 illustrating the catheter apparatus positioned within a vascular graft disposed in a blood vessel.
Figure 7:
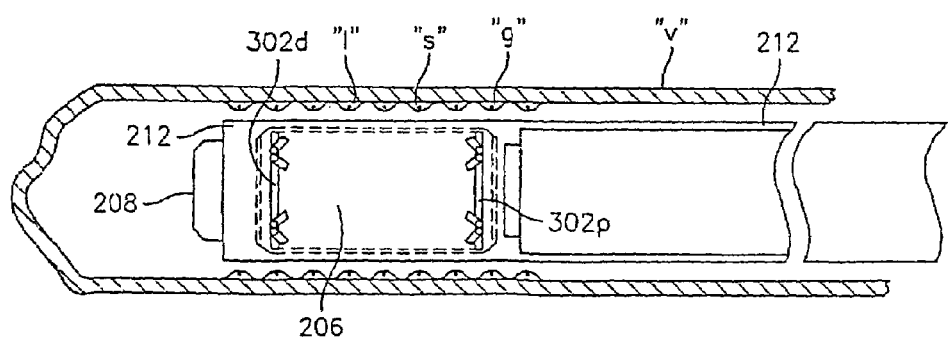
FIG. 7 is a side cross-sectional view further illustrating the catheter apparatus positioned within the vascular graft.
Figure 8:
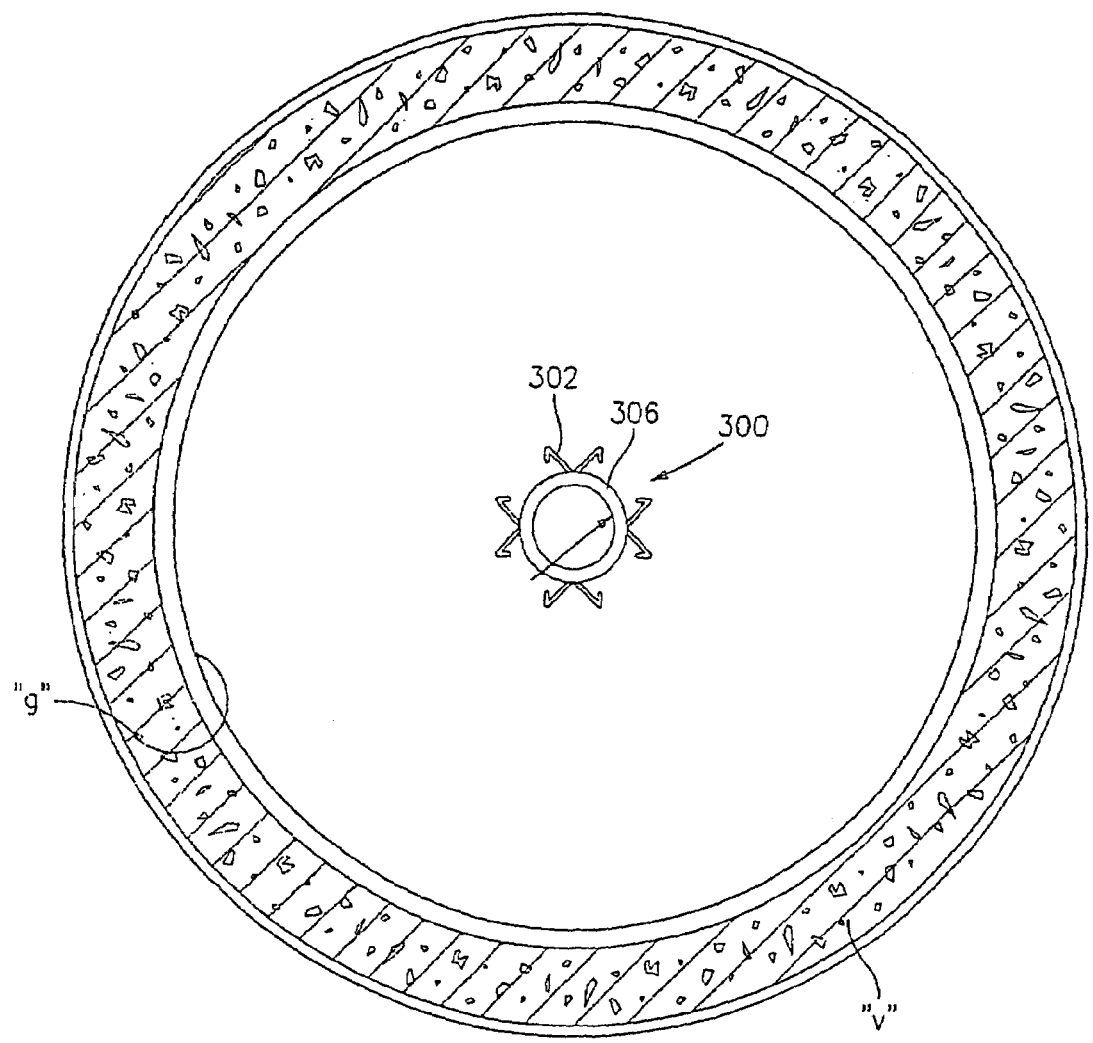
FIG. 8 is a view similar to the view of FIG. 6 illustrating the outer tube of the catheter apparatus in a retracted position to expose the staple array.

With particular reference to FIGS. 6-7, graft "g" (including a stent "s" embedded therein) is first positioned within the aneurysm site "l" of the blood vessel "v" by conventional means. Thereafter, catheter apparatus 200 is advanced through the femoral artery to the aneurysm site "l". Catheter 200 may be advanced with the assistance of a guide wire as is known in the art and manipulated to the desired location. Preferably, outer tube 212 of catheter 200 is in its advanced position as depicted in FIG. 7 enclosing staple array 300 (shown in phantom) thereby preventing inadvertent engagement of the staples 302 with the vessel wall during advancement. Catheter apparatus 200 is positioned within the graft "g" such that the proximal and distal staple sets 302p, 302d mounted to catheter balloon 206 are adjacent respective end portions of the graft "g". Upon reaching the desired location inside the blood vessel "v", a clamp or other means may be used to prevent further forward or upstream movement of the catheter 200. Thereafter, outer tube 212 is retracted to the position of FIG. 2 to expose staple array 300. FIG. 8 also schematically depicts in cross-section, outer tube 212 retracted to expose the staple array 300.

Figure 9:
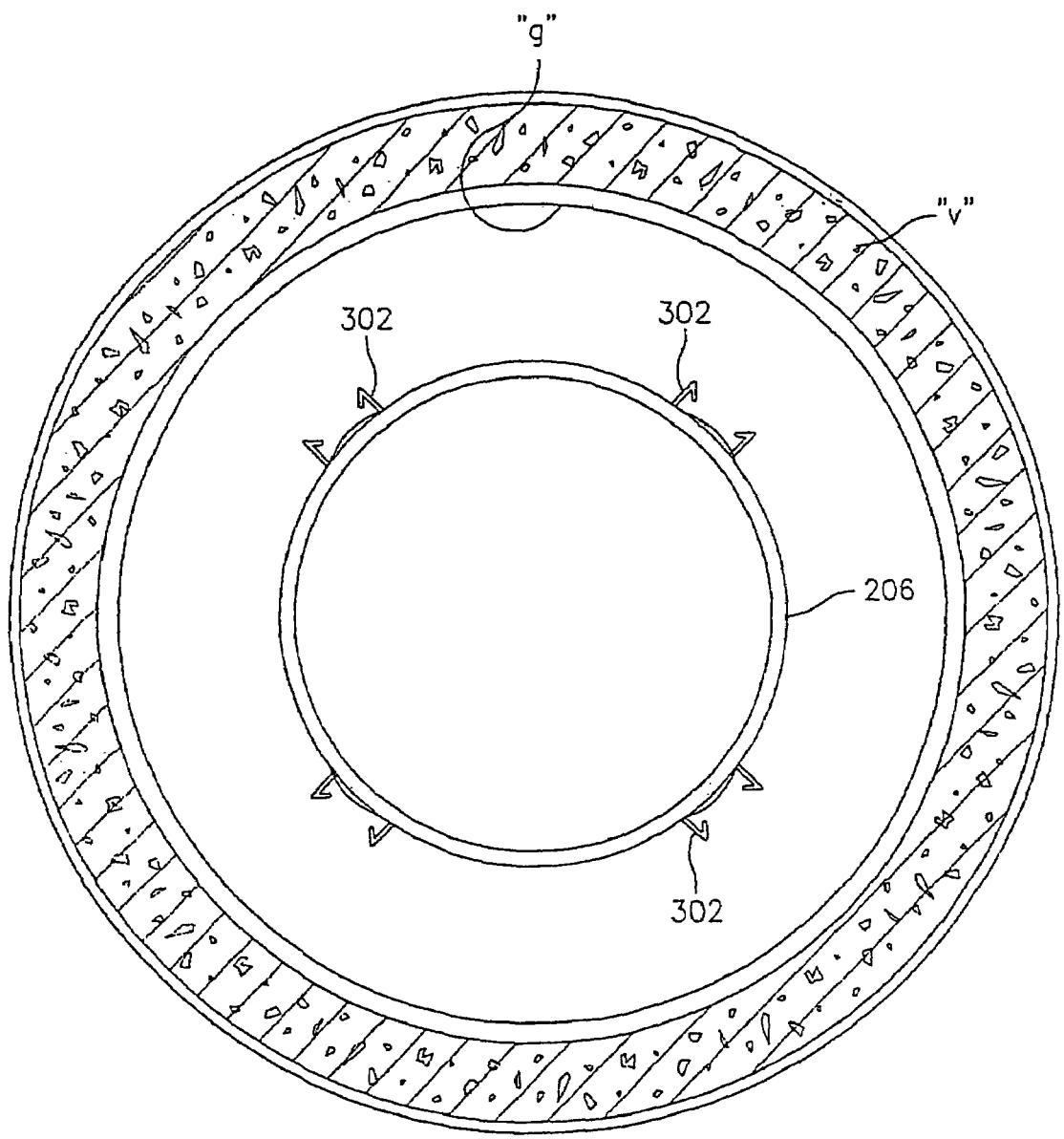
FIG. 9 is a view similar to the view of FIG. 8 illustrating expansion of the catheter balloon.
Figure 10:
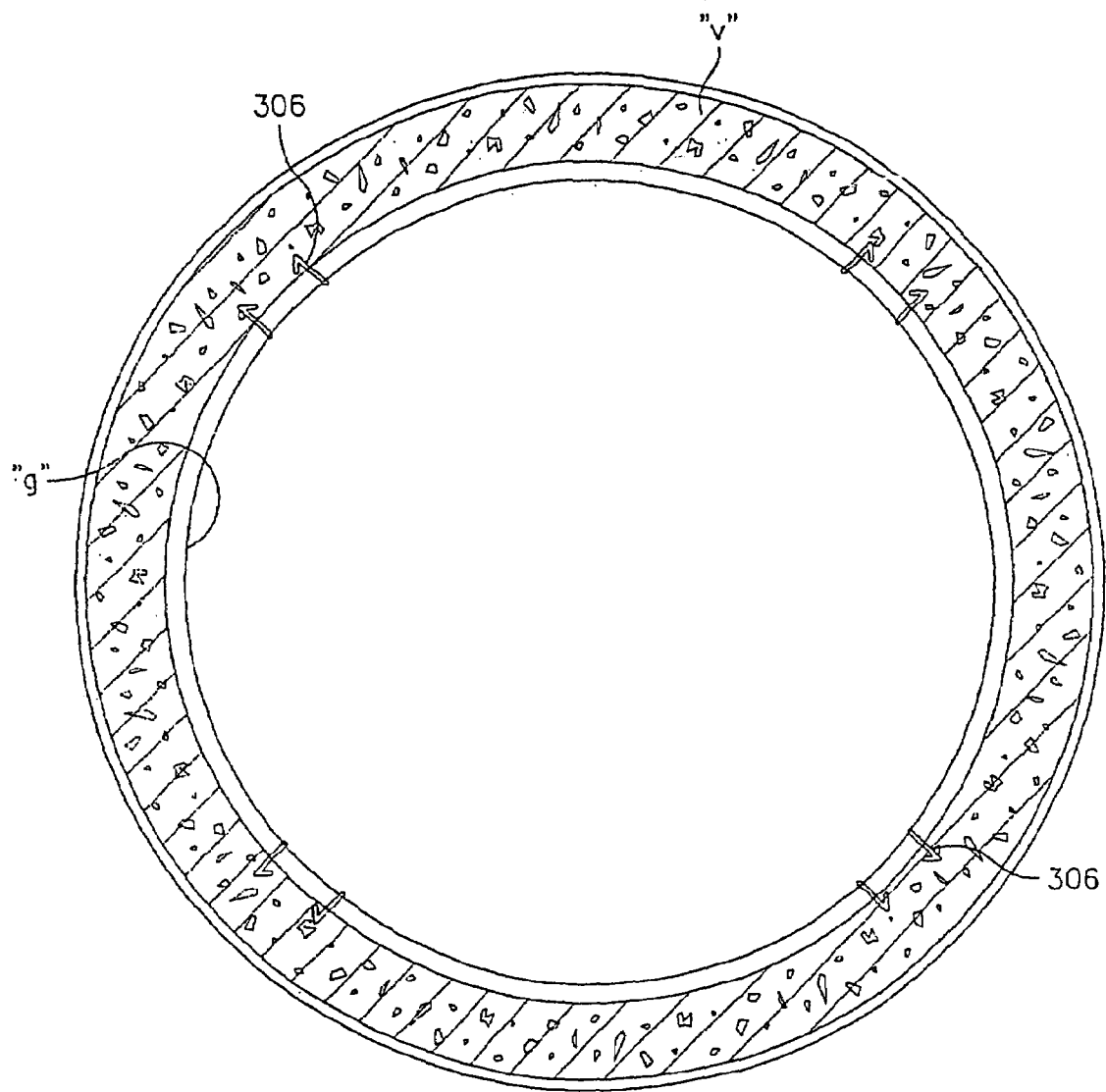
FIG. 10 is a view similar to the view of FIG. 9 illustrating the staples of the staple array deployed in the vessel wall.

With reference now to FIGS. 9-10, catheter balloon 206 is expanded from its initial position to its expanded condition through the introduction of injection fluids as previously discussed. Upon expansion, staple legs 306 of staples 302 are driven through the graft "g" to penetrate the vessel wall "v" without completely piercing the wall as depicted in FIG. 10. FIG. 10 depicts the catheter balloon 206 removed and staple array 300 deployed within the vessel wall "v". As appreciated, retaining hooks 308 of staple legs 306 facilitate retention of the staples 302 within the wall "v". Thereafter, catheter balloon 206 is deflated. Upon deflation, staple bases 304 of staples 302 are released from their adhesive mounting to catheter balloon 206. Catheter 200 is then removed from the vessel leaving the secured graft within the blood vessel "v".

It is appreciated that staples 302 may be deployed sequentially, e.g., with the distal staple set 302d deployed first followed by deployment of the proximal staple set 302p. In accordance with this method, outer tube 212 may be initially retracted to expose the distal staple set 302d and the catheter balloon 206 inflated to embed the distal staple set 302d in the vessel wall "w". Thereafter, outer tube 212 may be fully retracted to expose the proximal staple set 302p and the catheter balloon 206 inflated to deploy the staples 302. It is further envisioned that the stent/graft device may be mounted to catheter balloon 206 prior to introduction of the catheter 200 into the blood vessel. In this application, staple legs 306 of staples 302 penetrate the stent/graft to secure the stent/graft on catheter balloon 206 and outer tube 212 encloses the graft "g" during insertion through the body vessel "v". Inflation of catheter balloon 206 expands the stent/graft (in the case of mechanically deformable stents) and simultaneously embeds the staple legs within the vessel wall "v".

ALTERNATIVE EMBODIMENT(S)

Figure 11E:
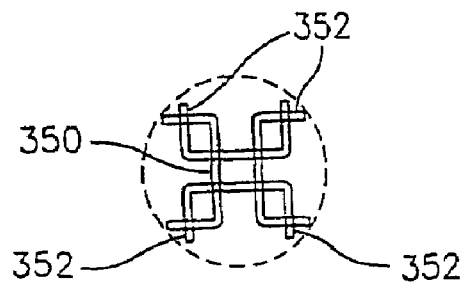
Figure 11F:
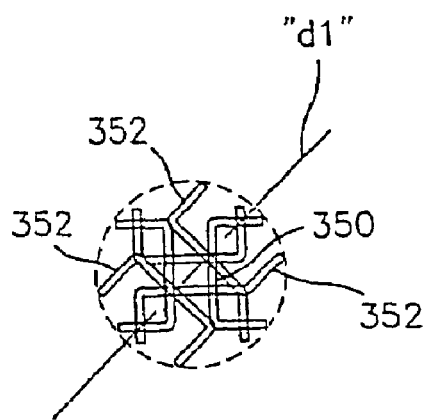
Figure 11G:
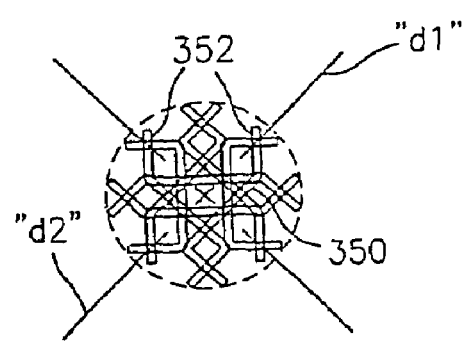

With reference now to FIGS. 11A-11G, it is envisioned that various multiple arrays of staples may be used in the system of the present invention. For example, FIG. 11A schematically depicts the use of two staples 350 which could be mounted on catheter balloon 206 in opposed relation as shown. In the embodiment of FIG. 11B, four staples 350 having staple legs 352 are preferably arranged in a circular side by side fashion around the catheter balloon 206. FIGS. 11C-11D illustrate the use of 6 and 8 staples respectively. In accordance with these embodiments, the additional staples would be arranged in superposed relation as shown along first and second diagonals "d1, d2". With the embodiment of FIG. 11D, two circular arrays of four staples each would be arranged in superposed relation to define the annular array. FIG. 11E illustrates a four staple array 350 that may be mounted on catheter balloon in which adjacent ends of the staples overlap. FIG. 11F is similar to the embodiment of FIG. 11E but adds an additional two staples arranged along a diagonal "d1" thereby totaling six staples. FIG. 11G illustrates a further alternate embodiment of FIG. 11F adding an additional two staples along diagonal "d2" to total eight staples. The number and arrangement of the staple arrays will depend on the size and intended application of the graft. Preferably, the staples of the aforedescribed arrays are adhered to each other through the use of an adhesive as discussed hereinabove to form a single unit which is subsequently adhered to catheter balloon 206. The overlapping array arrangement will provide for more closely spaced staples when deployed within the body vessel.

Figure 12:
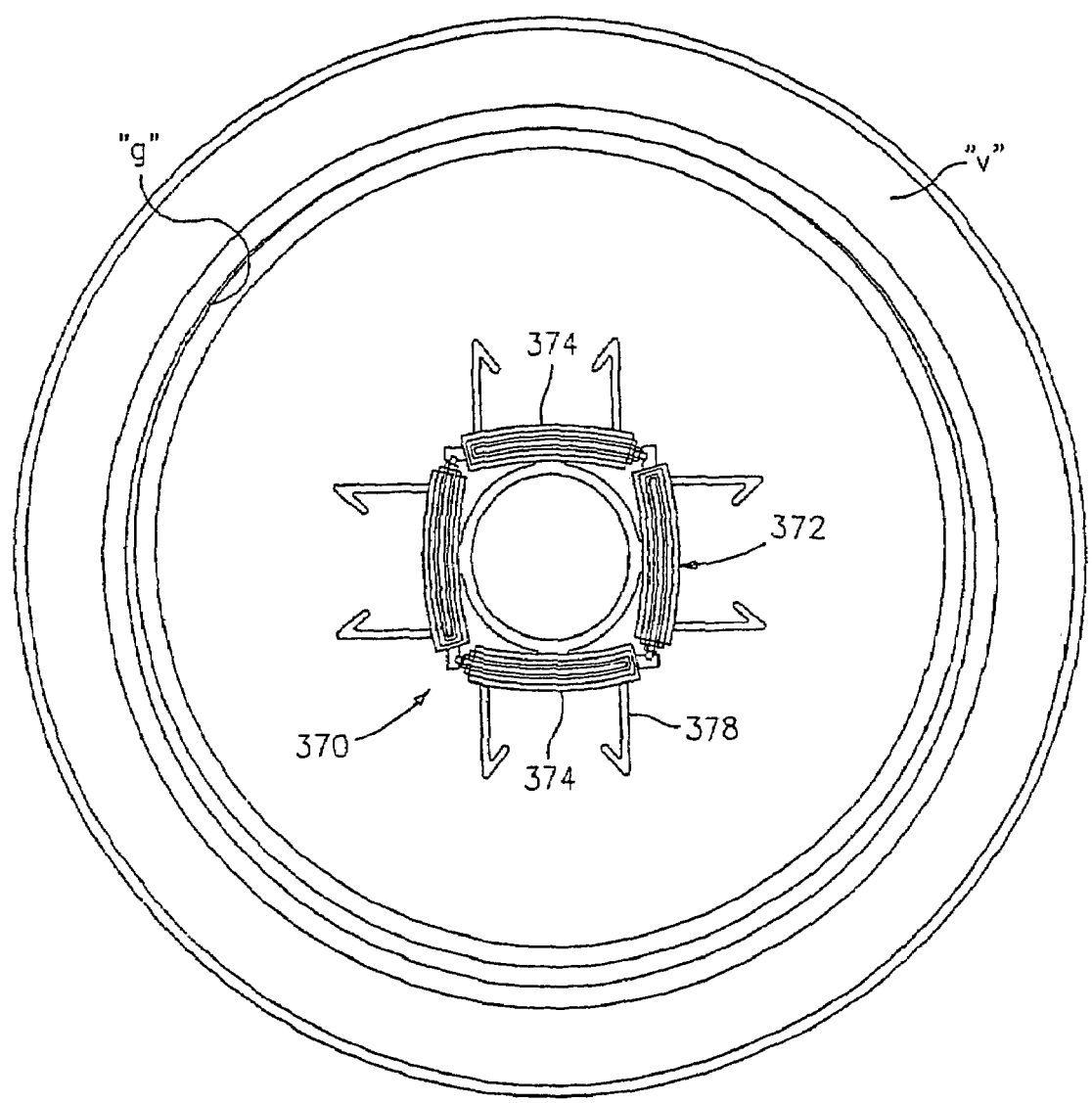
FIG. 12 is a schematic view illustrating an alternative embodiment of the staple array incorporating a telescoping staple arrangement.
Figure 13:
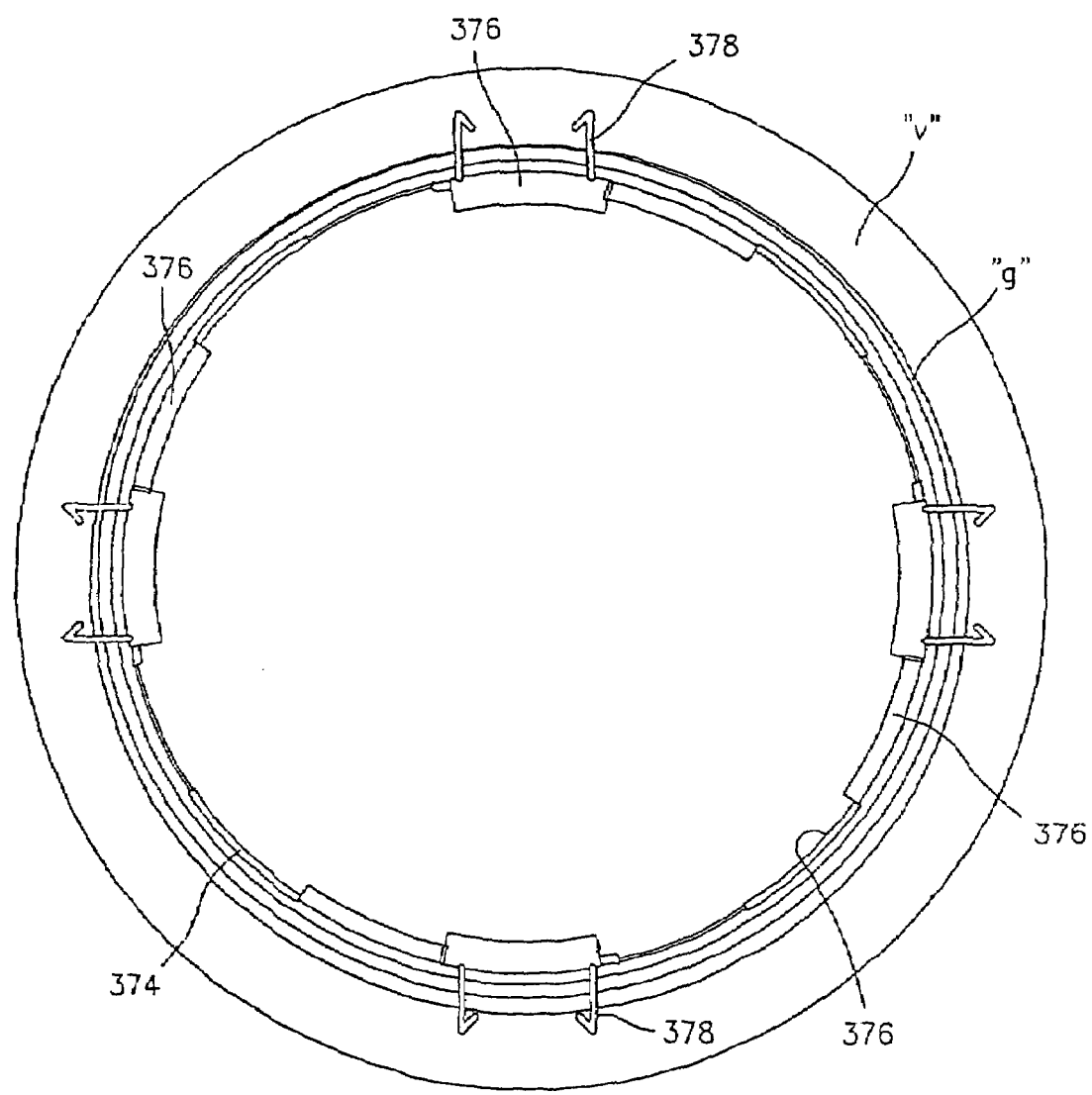
FIG. 13 is a schematic view illustrating the staple array of FIG. 12 deployed within the blood vessel wall.

FIGS. 12-13 illustrate another alternative embodiment incorporating a telescopic staple array 370. In accordance with this embodiment, each staple 372 of the annular array 370 includes a staple base 374 having a plurality of hollow telescoping members 376 arranged in telescopic relation. As depicted in FIG. 13, the telescoping members 376 extend outwardly from their telescopic arrangement upon expansion of catheter balloon 206 (not shown) to drive staple legs 378 into the vessel wall "w". The telescoping members 376 of each respective staple 370 are operatively connected to each other to permit such telescoping movement while maintaining connection between the members 376. Adjacent staples 372 are connected to each other along respective base members 374 with conventional means, e.g., bolt, hook, etc. . . . The staple array 370 may be adhered to the outer surface of catheter balloon with an adhesive as previously discussed.

Figure 14:
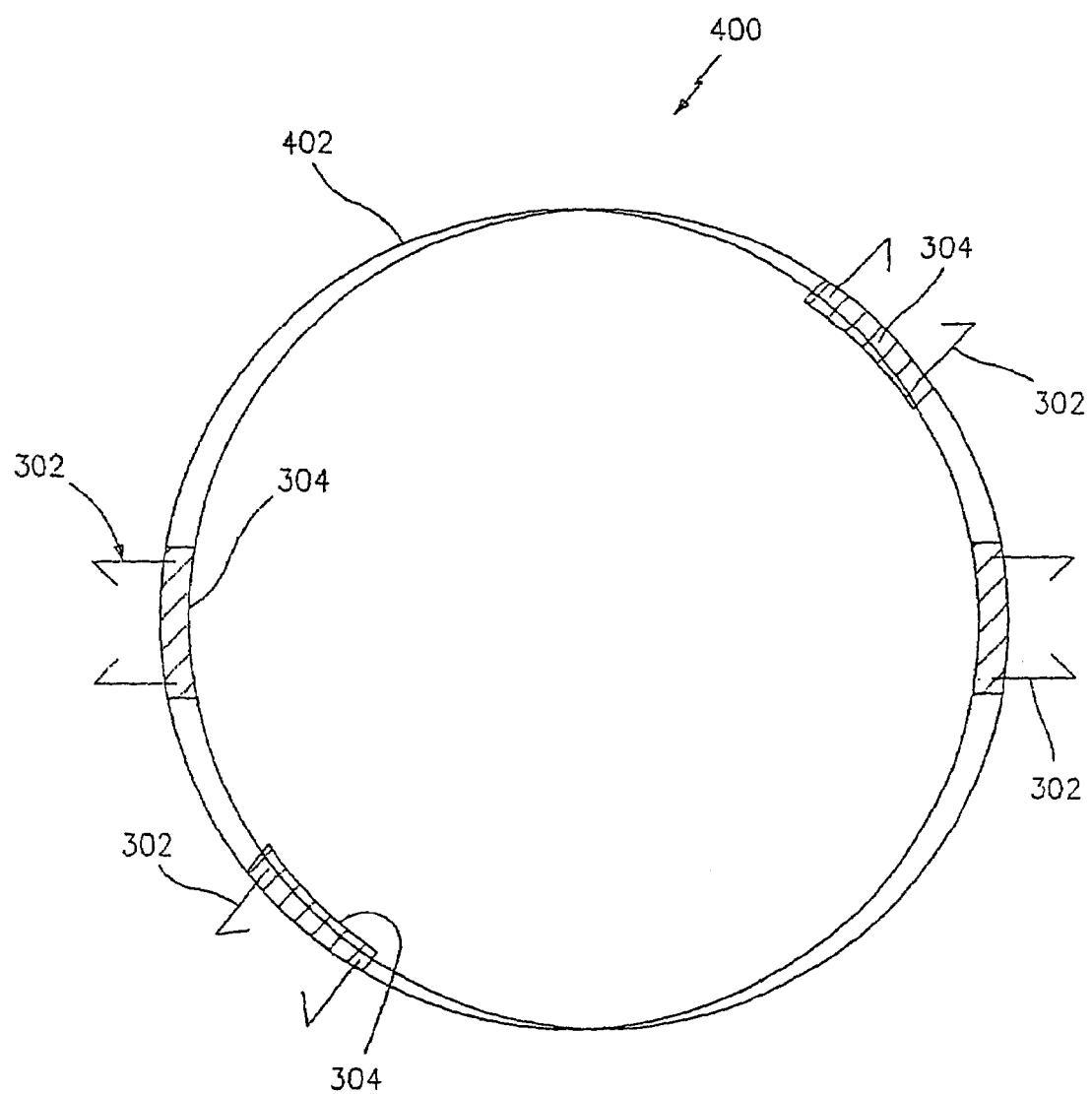
FIG. 14 is a schematic view illustrating another alternative embodiment of the staple array incorporating a biodegradable tape to which the staples are secured.
Figure 15:
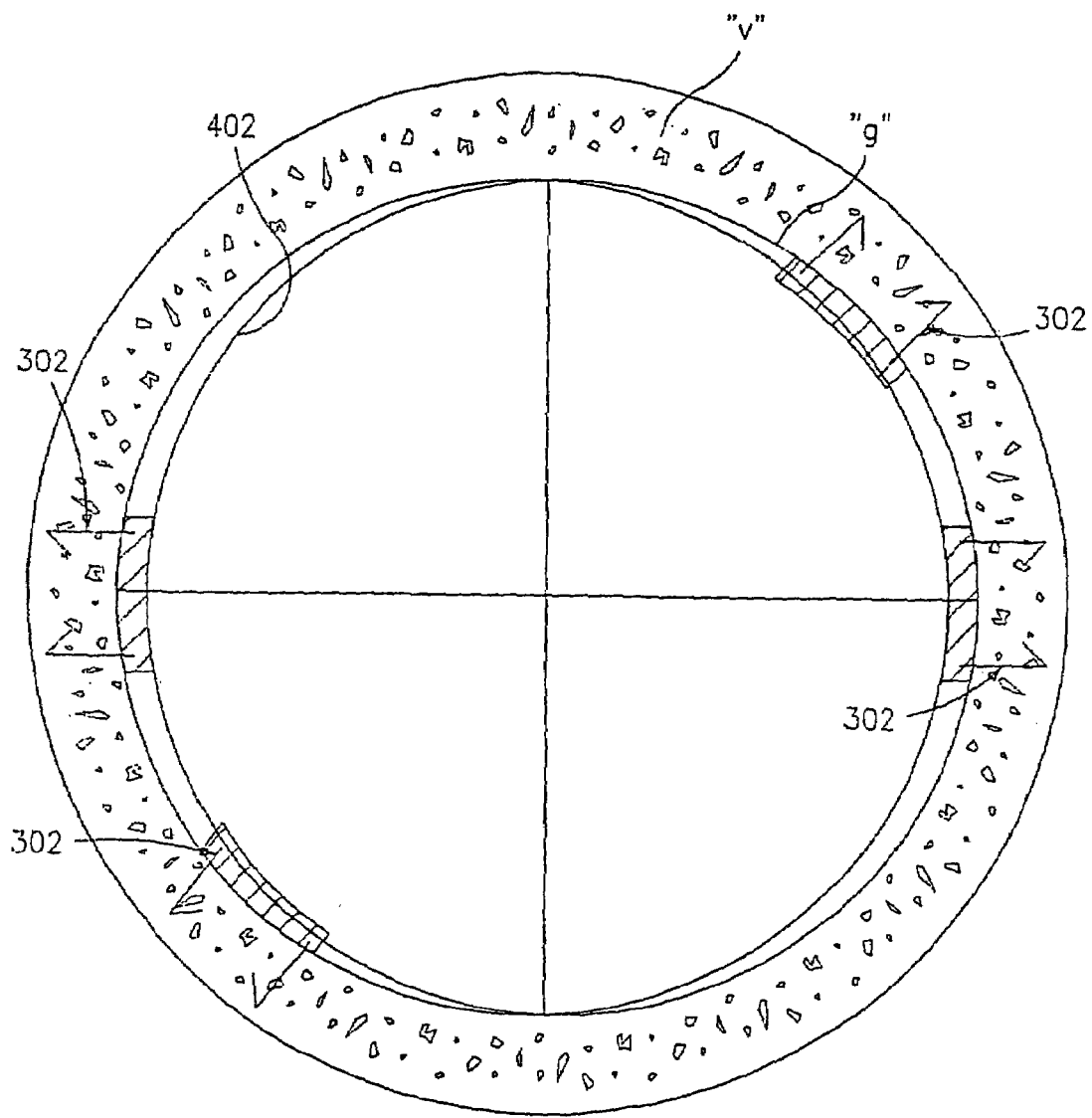
FIG. 15 is a schematic view illustrating the staple array of FIG. 14 deployed within the blood vessel wall.

With reference now to FIG. 14, another embodiment of the staple array for use with the system of the present invention is illustrated. Tape and staple array 400 includes a thin biodegradable/bioabsorbable polymer tape 402 defining a ring-like configuration as shown to which the staples 302 are attached. Examples of a suitable polymer tape include tapes fabricated from a polyglycolide and/or copolymers thereof. The staple base 304 of each staple may be adhered to polymer tape 402 with hyaluronic acid. The number and size of the staples as well as the diameter of the polymer tape 402 can be selected, as required. The polymer tape 402 is thin and flexible such that the staples 302 are assembled in the compact circular array as described above and may be adhered to catheter balloon 200. The entire assembly is positioned on catheter balloon 206 and deployed through expansion of catheter balloon 206. FIG. 15 illustrates the location of tape 402, staples 302, and graft "g" inside the blood vessel "v" after deployment. The ring shape of tape 402 maintains the staples in the appropriate position to engage and penetrate the vessel wall. The biodegradable/bioabsorbable polymer tape disintegrates over a period of time. The absorption rate of the polymer tape can be controlled through conventional means as appreciated by one skilled in the art.

Figure 16:
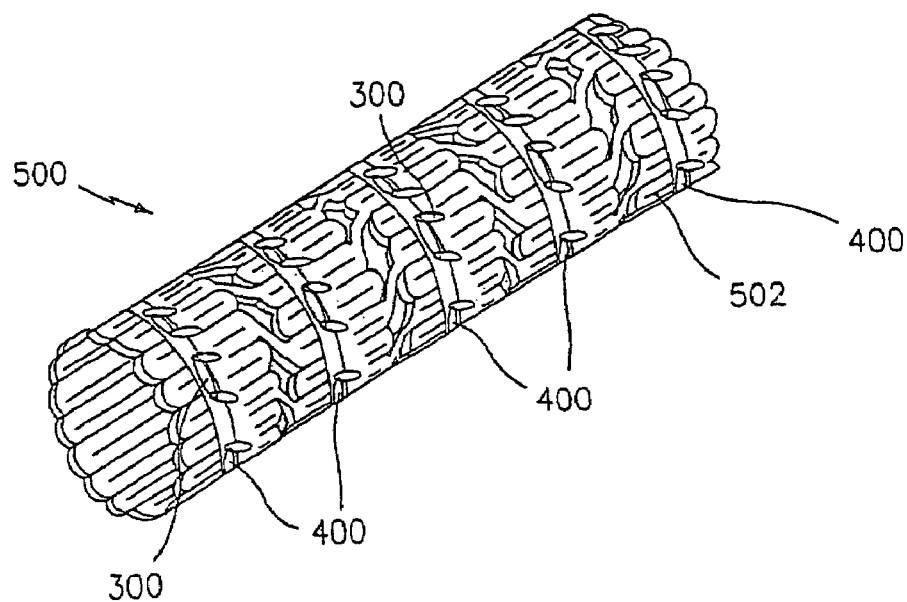
FIG. 16 is a perspective view illustrating another alternate embodiment including a stent and a plurality of biodegradable tapes with associated staples secured thereto.
Figure 17:
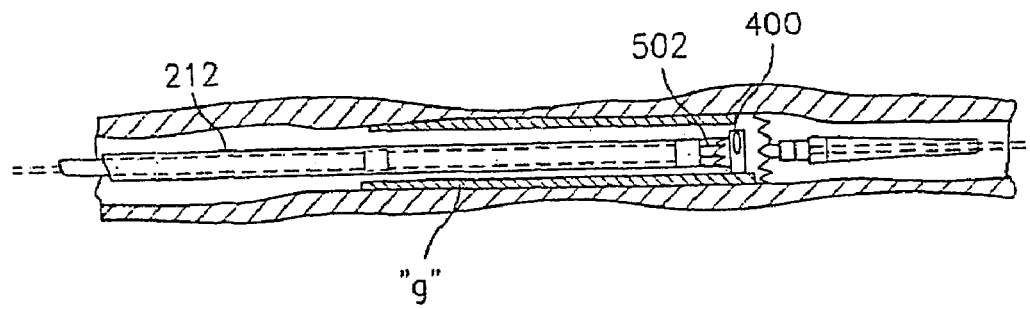
FIG. 17 is a view illustrating the stent and array mounted to the distal end of the catheter and inserted within the blood vessel.
Figure 18:
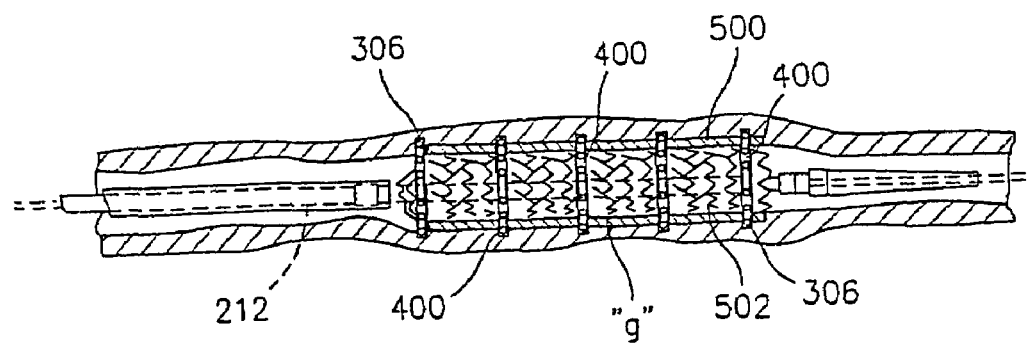
FIG. 18 is a view illustrating retraction of the outer tube of the catheter apparatus to deploy the stent and staple array.

FIGS. 16-18 illustrate an alternative embodiment utilizing the staple array 400 of FIGS. 14-15. In particular, stent and staple array device 500 includes a self-expanding stent 502 and a plurality of tape and associated staple arrays 400 disposed along the outer surface of the stent 502 at predetermined intervals. Stent 502 may be of the type disclosed in U.S. Pat. No. 6,019,778 to Wilson et al., the contents of which are incorporated herein by reference, and may be temperature responsive to assume its enlarged diameter upon deployment and exposure within the body vessel. Alternatively, stent 502 may be mechanically constrained in a reduced diameter condition whereby, upon release, the stent returns to its normal unstressed condition. A stent suitable for this use is disclosed in U.S. Pat. No. 6,165,200 to Lau, the contents of which are incorporated herein by reference. FIGS. 17-18 illustrate use of the device 502 with catheter 200. The device 500 may be mounted to the distal end of the catheter by conventional mechanical means, e.g., a friction fit. Preferably, the deployment catheter 200 has an outer tube 212 which longitudinally reciprocally moves in the same manner as discussed in connection with the embodiment of FIG. 1. Upon initial insertion within the blood vessel "v", the outer tube 212 is in its advanced position enclosing the device 500. When the device 500 is appropriately positioned within the graft "g", the outer tube 212 is retracted to enable the self-expanding stent 502 to expand sequentially to its expanded condition. FIG. 15 illustrates the outer tube 212 retracted to an intermediate position and FIG. 16 illustrates the outer tube at its fully retracted position. Upon expansion of the respective segments of the stent 502, the staples 302 of array 400 are driven through the graft "g" and embedded within the wall of the body vessel "v".

Figure 19:
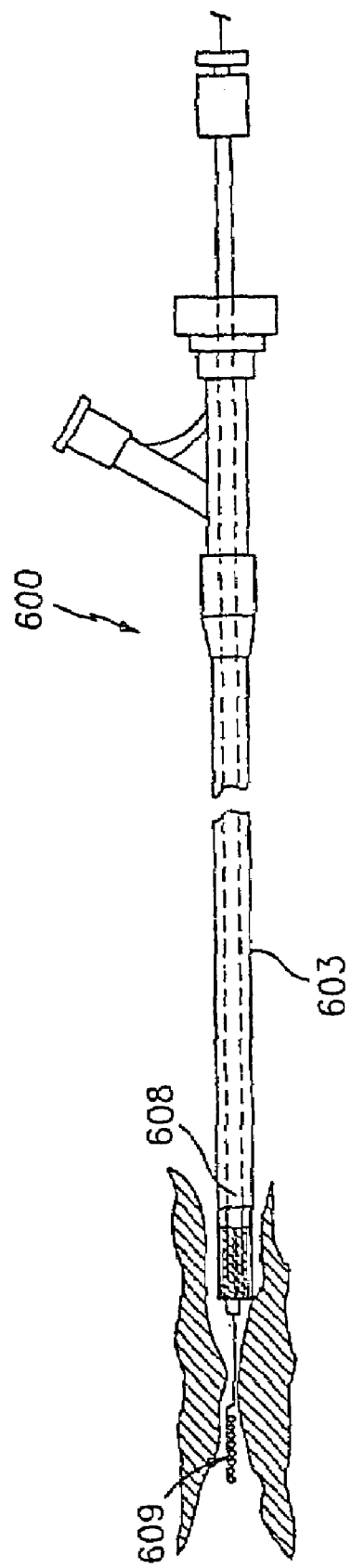
FIG. 19 is a side plan view of an alternate apparatus incorporating an umbrella mechanism for deployment of the staples for fixation of vascular grafts.
Figure 20A:
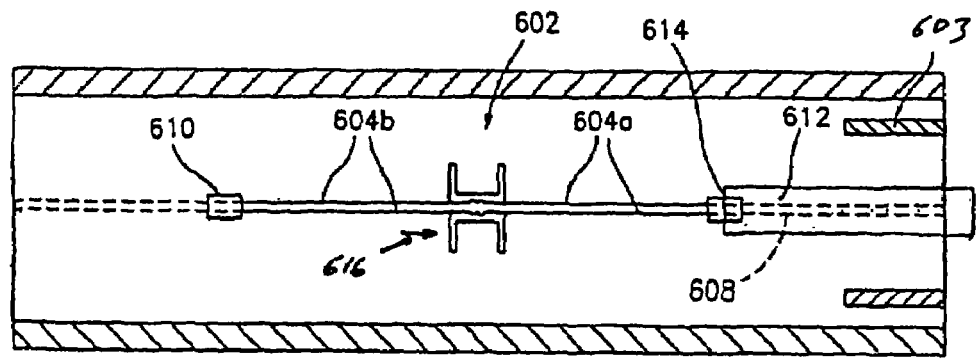
FIGS. 20A-20C are views illustrating a sequence of operation for deploying the umbrella mechanism.
Figure 20B:
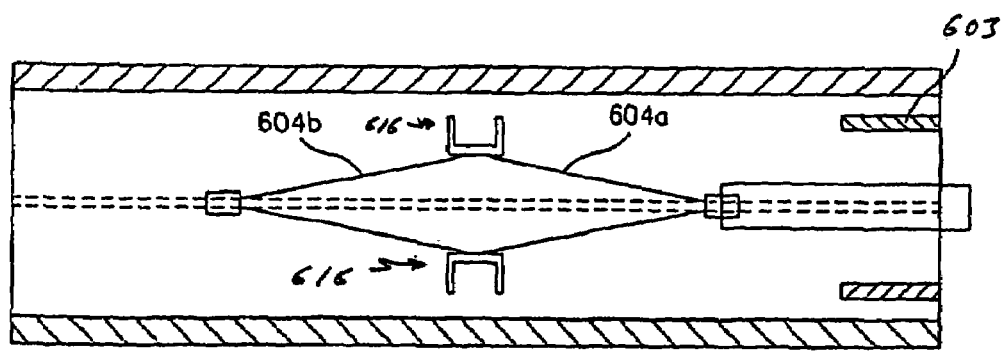
Figure 20C:
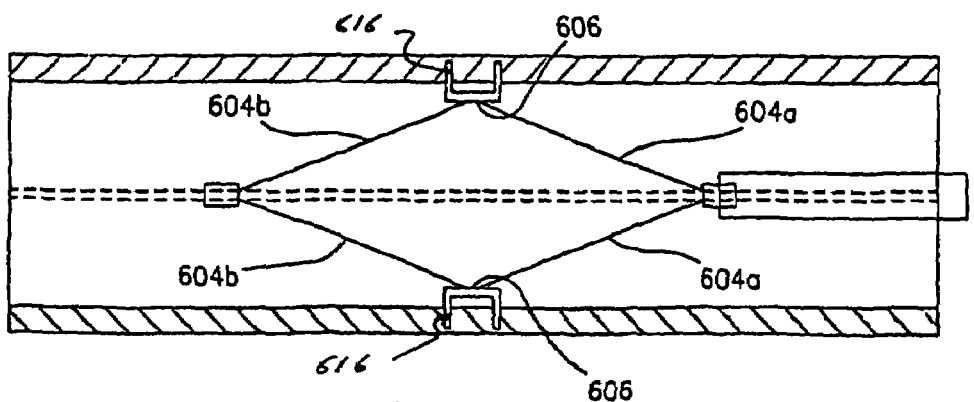
Figure 21:
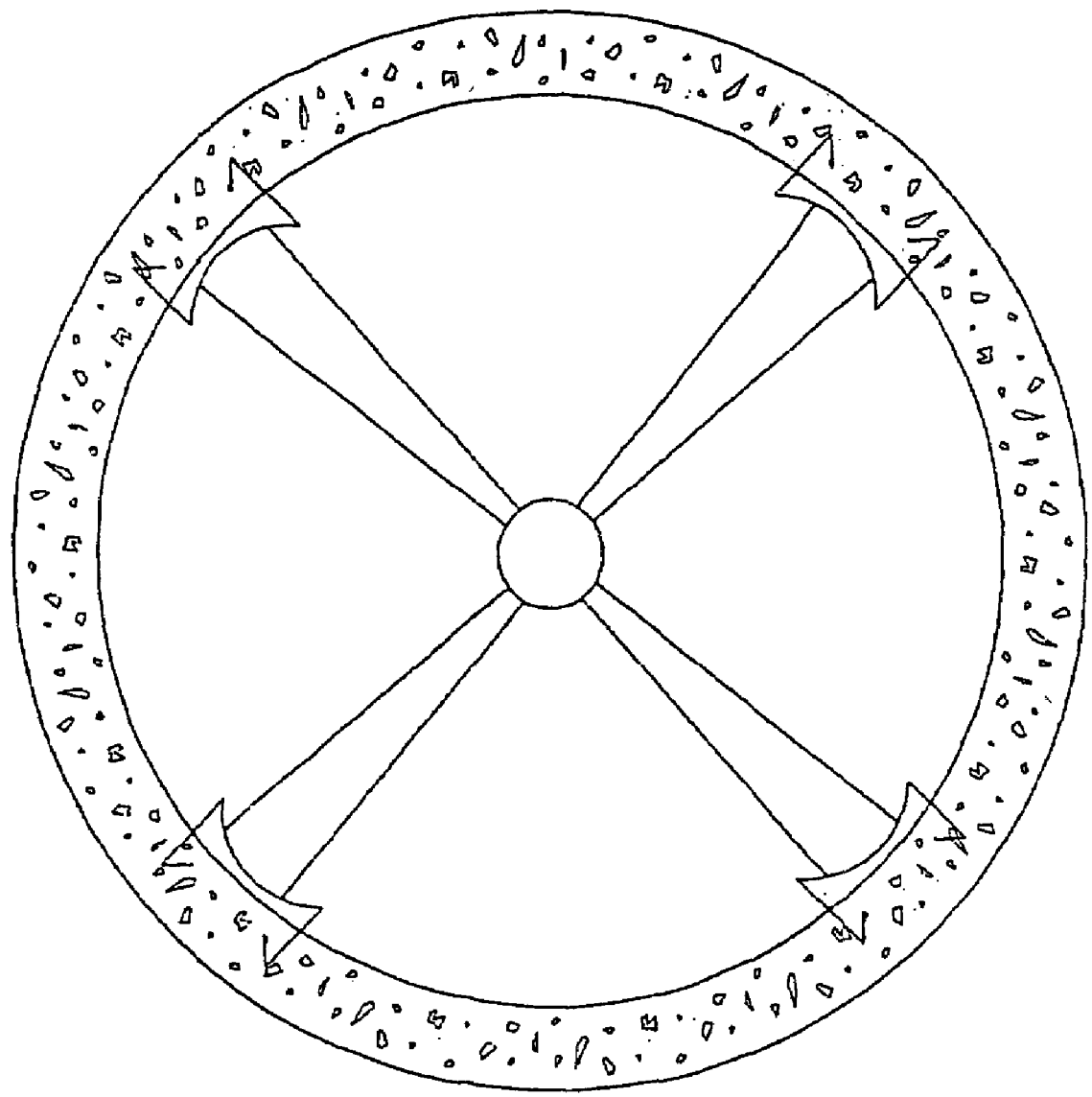
FIG. 21 is a schematic cross-sectional view illustrating the catheter apparatus positioned within a vascular graft and the umbrella mechanism fully deployed to drive the staples into the vascular wall.

FIGS. 19-21 illustrate an alternate apparatus for deploying a vascular graft. This apparatus 600 includes a catheter apparatus similar to the apparatus utilized in FIG. 1, but further incorporates an umbrella mechanism 602 for deploying the staples. The umbrella mechanism 602 involves a plurality of arms (spokes) 604 having respective proximal 604a and distal legs 604b connected to each other about a respective hinge schematically identified by reference numeral 606. In FIG. 19, umbrella mechanism 602 is shown confined within outer sheath 603 of catheter 600. A stationary central elongated member 608 extends through the catheter. The elongated member 608 may function as a guide wire and may possess a coiled end 609 as depicted in FIG. 19. The distal legs 604b of each arm 604 are connected to the central member 608 through hinge means, pivot means 610, etc. A drive member 612 is coaxially mounted about central member 608 and reciprocally moveable along the central member 608. The drive member 612 is operatively connected to proximal legs 604a of spokes 604 through hinge means 614, (or a pivot pin, etc.) as appreciated by one skilled in the art. The drive member 602 has handle 614 disposed at its proximal end adapted for engagement by the user. Drive member 612 moves between a proximal position corresponding to a non-deployed condition of the umbrella mechanism (FIG. 20A) through an intermediate position corresponding to a partially deployed condition of the umbrella mechanism (FIG. 20B) to a fully advanced position corresponding to a fully deployed condition of the umbrella mechanism (FIG. 20C).

Staples 616 are attached to the surface of the arms of the device adjacent hinge 606 with a glue, such as hyaluronic acid or mechanical interlocking as discussed in the prior embodiments. The staples 616 can be arranged in a compact assembly. Before deployment, the arms 604 of the umbrella mechanism are aligned to the axis and thus the device with the staples defines a reduced profile is compact perpendicular to the graft. FIG. 19 shows the device inside catheter sheath 603 before deployment of the staples. FIGS. 20A-20C illustrate the method of deployment of the staples. In these Figures, the graft is not shown. The catheter 600 is positioned at the desired location inside the blood vessel (after deployment of the vascular graft). The umbrella mechanism 604 is deployed from the outer catheter sheath 603 of the catheter by causing relative movement of the catheter sheath 603 with respect to central member 608 and drive member 612. For example, catheter sheath 603 may be retracted to expose umbrella mechanism 604. While maintaining central member 608 stationary, drive member 612 is advanced to drive umbrella arm outwardly. The arms of the device are pushed to deploy the staples in the radical direction (the force on the device are pushed to deploy the staples in the radial direction (the force on the device can be easily controlled). 3) As depicted in FIG. 21, the staple stems are driven through the graft and inside the blood vessel, once fixed inside the vessel wall, the arms are retracted back to the original position. FIG. 21 shows a side view of the umbrella device and the staples embedded inside the blood vessel.

Thus, the present invention provides a more effective system for positively securing vessel grafts within a body vessel. The annular staple arrays ensure fixation about the entire circumference of the graft. Moreover, the embedded characteristic of the staples of each array without penetrating through the vessel wall further reduces the potential for leakage at the fixation locations.

While the above description contains many specifics, these specifics should not be construed as limitations on the scope of the disclosure, but merely as exemplifications of preferred embodiments thereof. Those skilled in the art will envision many other possible variations that are within the scope and spirit of the invention

What is claimed is:

1. An apparatus for securing a vascular graft within a blood vessel, the apparatus comprising:
    a shaft dimensioned for passage within the blood vessel and having an expansion member, said expansion member movable between a contracted condition and an expanded condition; and
    a fastener array comprising a plurality of fasteners disposed about a peripheral portion of said expansion member, said plurality of fasteners being deployable into a wall of said blood vessel upon movement of said expansion member to said expanded condition thereof, to engage and to secure the vascular graft to the wall of the blood vessel,
    wherein, when the expansion member is in the contracted condition, fasteners of the fastener array are arranged in overlapping relation.

2. The apparatus according to claim 1, wherein each fastener of the plurality of fasteners has a telescopic base.

3. The apparatus according to claim 1, wherein each fastener of the fastener array is operatively connected to another fastener.

4. The apparatus according to claim 1, wherein said fasteners of said fastener array are releasably secured to said peripheral portion of said expansion member.

5. The apparatus according to claim 4 wherein the fasteners are releasably adhered to said peripheral portion of said expansion member with an adhesive.

6. The apparatus according to claim 2 wherein said fastener array defines a substantially annular arrangement whereby said fasteners are arranged about a periphery of said expansion member.

7. The apparatus according to claim 1 wherein said fasteners of said fastener array are connected to a biocompatible member, said biocompatible member being mounted about said peripheral portion of said expansion member.

8. The apparatus according to claim 7 wherein the biocompatible member is a biocompatible tape.

9. The apparatus according to claim 2, wherein the telescopic base of the fasteners permits telescoping movement while maintaining connection between adjacent fasteners of said fastener array when securing the graft.

10. The apparatus according to claim 1, wherein each fastener of said fastener array is a surgical staple having a base and penetrating legs extending from opposed ends of said base.

11. The apparatus according to claim 10 wherein said legs of each said staple define a length sufficient to penetrate through the vascular graft and lodge within the wall of the blood vessel without penetrating completely through the wall of the blood vessel.

12. The apparatus according to claim 1 wherein said expansion member is an inflatable balloon member.

13. The apparatus according to claim 1, wherein the expansion member is an umbrella mechanism.

14. The apparatus according claim 10, wherein progressive balloon inflation provides sequential deployment of the fasteners.

15. An apparatus for securing a vascular graft within a blood vessel, the apparatus comprising:
    an elongated shaft having proximal and distal ends, and defining a longitudinal axis, said elongated shaft being dimensioned for passage within the blood vessel;
    an expansion member supported at said distal end of said elongated shaft, said expansion member movable between contracted and expanded conditions; and a surgical staple array including a plurality of surgical staples arranged about a peripheral portion of said expansion member, a plurality of surgical staples being arranged in partial overlapping relation, said staples of said staple array being deployable into a wall of the blood vessel upon expansion of said expansion member;

wherein, when said expansion member and said surgical staple array are within the graft positioned within the blood vessel, said expansion member expands to deploy said surgical staples, thereby engaging said surgical staples with the vascular graft and the blood vessel to secure the vascular graft within the blood vessel.

16. The apparatus according to claim 15, wherein expansion of the expansion member arranges said surgical staples of said staple array to define an annular configuration.

17. The apparatus according to claim 16 wherein the plurality of surgical staples are, when the expansion member is in the contracted condition, positioned in a superposed, compacted relation wherein adjacent ends of said the surgical staples overlap.

18. A method for securing a vascular graft within a blood vessel, the method comprising the following steps:
accessing the blood vessel;
positioning the vascular graft at a predetermined location within the blood vessel;
introducing and moving a fastener array within the blood vessel, said fastener array including a plurality of surgical fasteners arranged about a longitudinal axis of said fastener array, said surgical fasteners having penetrating portions dimensioned to penetrate the vascular graft; and deploying said surgical fasteners of said fastener array radially outwardly relative to said longitudinal axis, wherein moving the fastener array within the blood vessel position disposes the fastener array at least partially within the vascular graft, and ends of said fasteners are overlapped prior to deploying said fastener array to provide a compacted fastener arrangement, said penetrating portions of said surgical fasteners penetrate the vascular graft and engage the blood vessel without completely penetrating the blood vessel, to thereby secure the vascular graft of the blood vessel.

19. The method according to claim 18, wherein said surgical fasteners of said fastener array are arranged with respect to each other to define a compacted substantially annular configuration whereby, upon deploying, said surgical fasteners expand and secure the substantially tubular graft to the blood vessel substantially along an outer peripheral graft wall.

20. The method according to claim 18, wherein said fasteners are sequentially deployed by an expansion member causing said surgical fastener to move radially outwardly into engagement through the vascular graft and into the blood vessel.

* * * * *